United States Patent [19]

Pignataro

[11] Patent Number: 5,697,979
[45] Date of Patent: Dec. 16, 1997

[54] METHOD AND APPARATUS FOR SECURING A HAIR PROSTHESIS TO THE HUMAN HEAD

[76] Inventor: Anthony S. Pignataro, 531 Center Rd., West Seneca, N.Y. 14224

[21] Appl. No.: 444,580

[22] Filed: May 19, 1995

[51] Int. Cl.$^6$ .................................................. A61F 2/10
[52] U.S. Cl. ................................................ 623/15; 606/187
[58] Field of Search .................. 623/15, 66; 606/187, 606/72, 73; 132/53, 56, 201

[56] References Cited

U.S. PATENT DOCUMENTS

| | | | |
|---|---|---|---|
| 3,662,766 | 5/1972 | Maassen et al. | |
| 3,694,819 | 10/1972 | Meyer | |
| 3,811,425 | 5/1974 | Widdifield | 128/1 |
| 3,858,247 | 1/1975 | Bauman | |
| 3,862,453 | 1/1975 | Widdifield | |
| 3,908,674 | 9/1975 | Kessler | 132/53 |
| 3,942,195 | 3/1976 | Bauman | |
| 4,372,317 | 2/1983 | Baumann | 128/330 |
| 4,632,100 | 12/1986 | Somers et al. | 128/92 |
| 4,676,802 | 6/1987 | Tofield et al. | 623/66 |
| 4,753,656 | 6/1988 | Tofield et al. | 623/15 |
| 4,793,808 | 12/1988 | Kirsch | 433/173 |
| 4,870,957 | 10/1989 | Goble et al. | 128/92 |
| 4,969,903 | 11/1990 | Valle | 623/15 |
| 5,060,677 | 10/1991 | Duffel | 132/201 |
| 5,102,414 | 4/1992 | Kirsch | 606/73 |
| 5,263,980 | 11/1993 | Leibinger et al. | 623/11 |
| 5,300,076 | 4/1994 | Leriche | 606/73 |
| 5,342,361 | 8/1994 | Yuan et al. | 606/72 |
| 5,370,662 | 12/1994 | Stone et al. | 606/74 |
| 5,474,555 | 12/1995 | Puno et al. | 606/72 |
| 5,545,224 | 8/1996 | Israelsen | 623/15 |

OTHER PUBLICATIONS

Liebinger, *Titanium EPITEC™ System for the Surgical Anchoring of Facial Prostheses*, Dept. of Oral and Maxillofacial Surgery, University Erlangen–Nurnberg, Gluckstrasse 11, D–8520 Erlangen, Developed in cooperation with M. Farmand, M.D., D.M.D., 75–80100.

Granstrom, et al., The Bone–Anchored Haring Aid and Bone–Anchored Epithesis for Congenital Ear Malformations, *Otolaryngology—Head and Neck Surgery*, vol. 109, No. 1, Jul., 1993.

Acuri, M., LaVelle, W.E., Fyler, E., Jons, R., "Prosthetic Complications of Extraoral Implants", Journal of Prosthetic Dentistry, vol. 69(3), pp. 289–292, 1993.

Jacobsson, M., Tjellstrom, A., Fine, L., and Andersson, H., "A Retrospective Study of Osseointegrated Skin–Penetrating Titanium Fixtures Used for Retaining Facial Prostheses," The International Journal of Oral & Maxillofacial Implants, vol. 7, No. 4, 1992, pp. 523–528.

Nerod, J.A., Carter, K.D., LaVelle, W.E., Fyler, A., and Branemark, P., "The Osseointegration Technique for the Rehabilitation of the Exenterated Orbit," Arch Opthalmol, vol. 109, Jul. 1991, pp. 1032–1038.

Stevenson, D.S., Proops, D.W., Wake, M.J.C., et al., "Osseointegrated Implants in the Management of Childhood Ear Abnormalities: The Initial Birmingham Experience," The Journal of Laryngology and Otology, Jun. 1993, vol. 107, pp. 502–509.

(List continued on next page.)

*Primary Examiner*—John G. Weiss
*Assistant Examiner*—Bruce E. Snow
*Attorney, Agent, or Firm*—Banner & Witcoff, Ltd.

[57] ABSTRACT

The present invention addresses the disadvantages of the prior art by using an osseointegrated mounting structure to secure the hair prosthesis to the scalp. This structure comprises an implant adapted for implantation within the cranial bone or skull. The implant is secured to the skull by threading into the bone. The implant includes a threaded central cavity. An abutment is attached to the implant and positioned to extend out of the scalp. The abutment includes a threaded portion that fits within the threaded cavity of the implant. The abutment creates a ball and socket joint with a retention attachment in a manner that allows the retention attachment to be removed. A moldable interface is secured to the retention attachment and the hair prosthesis whereby the hair prosthesis can be secured to the head by inserting the retention attachments into the abutment.

15 Claims, 1 Drawing Sheet

OTHER PUBLICATIONS

Jensen, O.T., Brownd, C., Blacker, J., *"Nosofacial Prostheses Supported by Osseointegrated Implants,"* The International Journal of Oral & Maxillofacial Implants, vol. 7, No. 2, 1992, pp.203–211.

Brandy, D.A., *"Extensive Scalp Lifting as a Reconstructive Tool for a Large Scalp Defect,"* J. Dermatol. Surg. Oncol. 18:806–811, 1992.

Kabacker, S.S., *"JuriFlap procedure for the Treatment of Baldness,"* Arch. Otolaryngol. 105:509–514, 1979.

Kabacker, S.S., Kridel, R.W.H., Krugmen, M.E., Swenson, R.W., *"Tissue Expansion in the Treatment of Alopecia,"* Arch. Otolaryngol. Head and Neck Surg. 112:720–725, 1986.

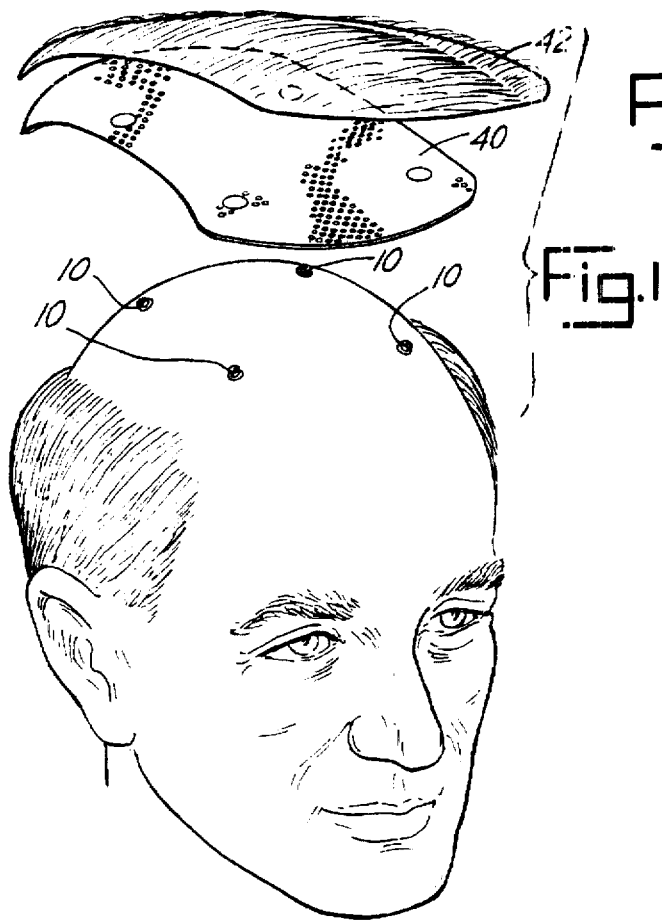
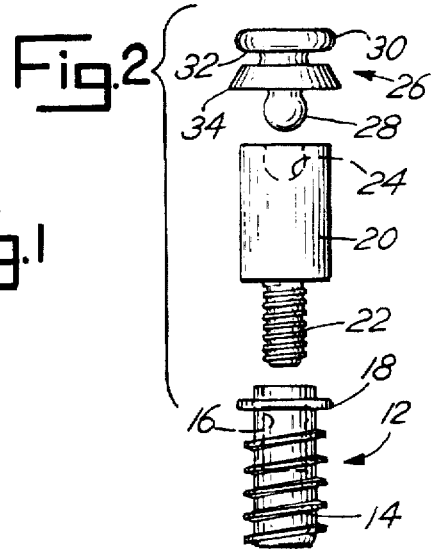
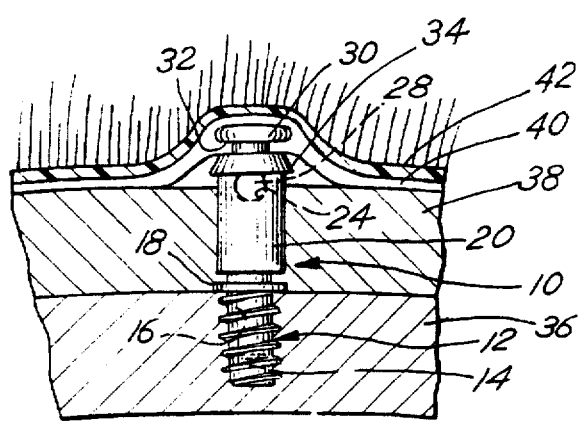
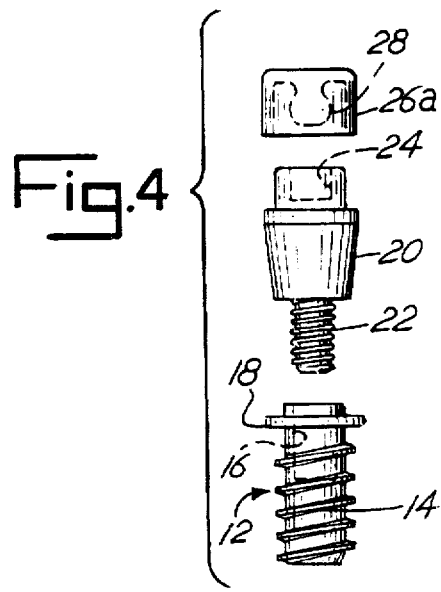

1

METHOD AND APPARATUS FOR SECURING A HAIR PROSTHESIS TO THE HUMAN HEAD

BACKGROUND OF THE INVENTION

1. Field of the Invention

The present invention relates to the field of mechanisms for securing hair pieces and wigs to the human head.

2. Description of the Prior Art

Over the years there have been numerous methods proposed and used for securing a hair prosthesis to the human head. Among these is U.S. Pat. No. 3,694,819 issued to Meyers which teaches a plurality of anchor members embedded in the scalp and a like number of attachment members connected to the hair piece such that when the hair piece is positioned on the scalp, the attachment members are latched into the anchoring members. Meyers teaches an anchoring member that is surgically implanted into the scalp tissue above the aponeurosis which lies under the topmost scalp tissue. Its anchor element includes a composite layer which allows an integral bond to form between the human tissue and the anchor element.

Widdifield, in U.S. Pat. No. 3,811,425 and U.S. Pat. No. 3,862,453 teaches methods and apparatuses for mounting hair prostheses including two different embodiments. The first embodiment employs a series of stainless steel anchors embedded in the fatty portion of the human scalp which are then attached to a hair mounting base. This hair mounting base can include either a stainless steel wire mesh or a plastic framework contoured to fit the scalp made from a polypropylene material. The second embodiment includes an implant which is placed on the skull and protrudes through the top of the scalp. The hair piece is then connected directly to the implant through various methods including a screw, Velcro or magnetic disk.

Kessler in U.S. Pat. No. 3,908,674 teaches the use of a suture method for attaching a hair piece that includes a ribbon-like border. In the method of Kessler, sutures are placed through the scalp and pass through openings in the ribbons of the hair piece and then are put in locking engagement with the ribbon.

Tofield et al. in U.S. Pat. Nos. 4,678,802 and 4,753,656 teaches an implant method for attaching the hair prosthesis in which the implant is placed in a marsupium or pouch of skin which is created by a inverse skin graft.

While each of these prior art methods has some advantages, they each have encountered several disadvantages. These disadvantages include: an inability to easily remove the hair piece; infection resulting from the moveability of the surgical implants mounted in soft tissue; infection, bleeding and scaring resulting from sutures working through the skin; the inability to adequately secure the hair piece to the implant; and an inability to allow the scalp to adequately breathe.

Separate from the field of hair prosthesis, the field of osseointegration has been developed. Osseointegration technology has been used for several years to attach prostheses to replace missing teeth. Recent advances in extraoral applications of osseointegration and prostheses have led to the replacement of lost eyes, and ears, as well as other nasofacial defects, due to trauma or surgical exenteration. This technique has not been used in the past in connection with devices that are useful in securing a hair prosthesis.

SUMMARY OF THE INVENTION

The present invention addresses the disadvantages of the prior art by using an osseointegrated mounting structure to secure the hair prosthesis to the scalp. This structure comprises an implant adapted for implantation within the cranial bone or skull. The implant is secured to the skull by threading into the bone. The implant includes a threaded central cavity. An abutment is attached to the implant and positioned to extend out of the scalp. The abutment includes a threaded portion that fits within the threaded cavity of the implant. The abutment creates a ball and socket joint with a retention attachment in a manner that allows the retention attachment to be removed. A moldable interface is secured to the retention attachment and the hair prosthesis whereby the hair prosthesis can be secured to the head by inserting the retention attachments into the abutment.

The present invention also includes methods for the installation of the osseointegral mounting structures including the implantation of the implant, the attachment of the abutment and the securing of the hair prosthesis with the retention attachments.

The present invention is a novel option for hair replacement. It offers several advantages. The patient can be assured of a full head of hair without the risks of conventional hair-replacement surgery, i.e., necrosis, infection, cosmetic deformities, scarring, stretchback, slot formation, and lack of sufficient donor hair.

Other advantages of the present invention include the elimination of many of the deterrents to conventional hair-replacement prostheses-namely, their untimely detachment. Increased retention and stability allow one security while swimming, when exposed to high winds or during intimate situations.

A further advantage for the patient who currently wears a hair prosthesis is that he/she may continue to wear a hair prosthesis through all stages of the process.

Yet a further advantage of the present invention is that the implantation is fully reversible in that the implants can be removed.

Still another advantage of the present invention is the ease with which the system is maintained. Simple washing of the scalp with soap or shampoo is all that is required.

Yet another advantage of the present invention is that it provides a mechanism for the consistent placement of the hair prosthesis day after day.

It is an object of the present invention to provide an improved system for securing a hair prosthesis to the head. This system includes at least one osseointegral mounting structure upon which a hair prosthesis that has been affixed to a moldable interface can be mounted.

It is another object of the present invention to provide an osseointegral hair prosthesis system that comprises an implant, an abutment that attaches to the implant, a retention attachment that can be removably secured to the abutment, a moldable interface between the retention attachment and the hair prosthesis and a hair prosthesis attached to the moldable interface.

It is a further object of the present invention to provide a system for securing a hair prosthesis that will firmly hold the prosthesis in place in all kinds of conditions.

It is yet a further object of the present invention to provide a system for installing a series of rigid mounts to support a hair prosthesis and a mechanism to attach the prosthesis to the mounts to provide the appearance of a natural head of hair.

BRIEF DESCRIPTION OF THE DRAWINGS

FIG. 1 is a perspective of a human head illustrating the location of the osseointegral mounting structure on the scalp and the relative relationships of the moldable interface and the hair prosthesis.

FIG. 2 is an exploded diagram illustrating the relationship of the parts of the osseointegral mounting structure.

FIG. 3 is a cross sectional diagram illustrating the position of the osseointegral mounting structure when it is has been installed in the cranial bone.

FIG. 4 illustrates an alternative embodiment of the osseointegral mounting structure.

DETAILED DESCRIPTION OF THE INVENTION

The present invention relates to methods and mechanisms for securing a hair prosthesis to the human head. In the preferred embodiment, the mechanism of the present invention consists of three elements: the hair prosthesis 42, a moldable interface 40 and an osseointegral mounting structure 10. The osseointegral mounting structure is implanted into the skull 36 and passes through the scalp soft tissue 38. Referring to FIG. 1, in a preferred embodiment, there are a plurality of osseointegral mounting structures 10 implanted into the skull. The preferred number of such structures 10 is four, although fewer or more structures 10 may be appropriate with respect to a given patient. FIG. 1 illustrates the location of the various osseointegral mounting structures 10 in the human head.

FIG. 1 also illustrates how the moldable interface 40 is positioned with respect to the mounting structures 10. As can be seen in FIG. 1, the moldable interface 40 is shaped to match the shape of the patient's head. The interface 40 is then attached to a retention attachment match the shape of the patient's head. The interface 40 is then attached to a retention attachment 26 which can be secured to the osseointegral mounting structures 10. The moldable interface 40 should be biocompatible, and is preferably a plastic material in the form of a plastic mesh. Such material allows the scalp to continue to breathe while also providing an effective interface between the rigid osseointegral mounting structures 10 and the pliable hair prosthesis 42. In a preferred embodiment, the moldable interface 40 is a thermoplastic material that becomes moldable when heated and is rigid at room temperature. A preferred material for the moldable interface 40 is manufactured by WFR Aquaplast Corporation of Wyckoff, N.J., and sold under the tradename Optimold®. Optimold® is a semi-synthetic plastic material which can be custom molded to the individual patient's scalp when heated. Moreover, when Optimold® is cooled, it will become rigid in the proper configuration. Once the moldable interface 40 is properly formed it is a simple task to either bond or sew the hair prosthesis 42 to the moldable interface 40.

In an alternative embodiment, the moldable interface may be integral to the hair prosthesis. In this embodiment there is no need to attach a conventional prosthesis 42 to the interface 40, because the interface 40 itself would be the prosthesis. In other words, the hair is mounted directly to the moldable interface 40 instead of a standard toupee base. This alternative structure eliminates the need for a separate interface 40 and hair prosthesis 42.

Referring now to FIG. 2, the osseointegral mounting structure 10 is illustrated in detail. In a preferred embodiment, the osseointegral mounting structure 10 includes three elements: an implant 12, an abutment 20 and a retention attachment 26. The implant 12 is of an appropriate size to provide a secure mount in the cranial bone or skull 36. Implant 12 is 36. The implant 12 further has an extending flange 18 which provides a dual function of providing flats for application of the tool that is used to drive the implant 12 into place and providing a surface which can interface with the surface of the skull 36 once the implant 12 is in place. The implant 12 further includes a threaded cavity 16 which is designed to receive the abutment 20.

The abutment 20 at one end has a threaded shaft 22. This threaded shaft 22 is adapted to be secured into threaded cavity 16. At its other end, the abutment 20 defines a socket 24. This socket 24 is adapted to receive a ball-shaped structure and create a ball and socket snap fit joint.

The retention attachment 26 is preferably provided with a ball-shaped end 28 which fits into the socket 24 of the abutment 20. The resultant ball and socket joint results in the retention attachment 26 being removably secured in the abutment 20. In a particularly preferred embodiment, the ball 28 of the retention attachment 26 is removable and replaceable. This allows for simple repair of the retention attachment 26 should it become worn through use.

The retention attachment 26 is further provided with a beveled washer 34 which rests upon the uppermost surface of the abutment 20 when the retention attachment 28 is engagement with the abutment 20. This washer 34 provides resistance against excessive movement of the ball and socket joint created by ball-shaped end 28 and socket 24. The retention attachment 26 also preferably includes a cap 30 which defines a lip 32. As can be more clearly seen in FIG. 3, the cap 30 in combination with the lip 32 provides a means for attaching the moldable interface 40 to the retention attachment 26. Specifically, the moldable interface 40 can be crimped around the cap 30 under the lip 32. This crimping in combination with a glue secures the interface 40 to the retention attachment 26.

FIG. 3 provides a cross-section of the hair replacement system of the present invention. FIG. 3 illustrates the osseointegral mounting structure 10 implanted in the skull 36. The threaded portion 14 of the implant 12 is implanted in the skull 36. This implantation allows for a secure affixation of the osseointegral mounting structure 10 to the patient's head. This is especially true since in other osseointegral applications it has been shown that bone grows around the implant, further securing it in place. Once the implant 12 is in place, the abutment 20 is then attached to the implant 12 by threading the threaded shaft 22 into the threaded cavity 16. When in place, the abutment 20 will extend above the soft scalp tissue 38. The retention attachment 26 is then snapped into the abutment 20 securing the hair prosthesis 42 to the head.

It should be understood that the osseointegral mounting structure 10 may take on different forms without varying from the scope and spirit of the present invention. For example, the retention attachment 26 may be shaped differently. As opposed to defining a cap 30 and a lip 32 in conjunction with the beveled washer as illustrated in FIGS. 2 and 3, the retention attachment 26 may be formed more of a plastic cap which fits over the edge of the abutment 20 in a snapping manner. Such alternative structure is illustrated in FIG. 4 with the retention attachment 26a fitting over the abutment 20. An attachment 26 like that shown in FIG. 4 is commercially available from ERA and sold through APM—Steingold of Littleboro, Mass. The embodiment illustrated in FIG. 4 creates a joint which is more akin to a standard snap. Similar modifications can be made without varying from the invention.

While a retention attachment 26 which creates a snap fit is preferred, other types of attachments can be used and remain within the scope of the present invention. These attachments include loop and hook materials such as Velcro®, adhesives including glues, screws, pins, magnets and double sided tape.

A preferred process for implanting the osseointegral mounting structure 10 is described herebelow. The entire process involves three stages. During stage one, the implant 12 is inserted into the skull or cranial bone 36. During stage two the abutment 20 is attached to the implant 12. After a brief healing period, the hair prosthesis 42/moldable interface 40 is applied at stage three. It will be appreciated that adequate healing time should be allotted between each of the stages.

Stage 1

The patient's scalp is marked at the four points of implant 12 insertion. After sterile prepping and draping, the area is locally anesthetized with 2% lidocaine with 1/100,000 epinephrine. A #10 blade is used to incise the scalp 38 approximately 2.5 cm in length. The incision is carried straight down to and including the periosteum. A periosteal elevator is used to completely denude the bone surface. A small clamp is then used to provide exposure and compression hemostasis. An initial pilot hole is then drilled into the bone 36. All drill bits and taps employ a depth guard to insure against over drilling and possible intracranial injury. Following the initial pilot hole a series of progressively enlarging taps are used to carve an exact compliment of the threads on the thread section 14 of the implant 12. Preferably, very slow drill rotation (15 to 20 rpm) and sufficient irrigation are used while drilling to prevent thermal damage to the osteocytes. The implant 12 can then be exactly threaded into the tapped hole. A temporary healing cap is placed on the implant 12 and the skin is closed in layers. A sufficient healing period, about a twelve weeks, is allowed for osseointegration, i.e., bone growth around the implant 12.

Some concerns arise with respect to intrusion into the cranial vault as a result of the implant 12. Radiographs of fifty patients' heads were analyzed for bone thickness. The results are given in Table 1. As can be seen in all areas of cranial bone, the depth range was no less than 4 mm. The average (mean) depth is no less then 7.0 mm. The implants used in the invention are preferably about 3.5 mm in depth. At this depth there is little to no risk of entering the cranial vault.

TABLE 1

| Cranial Bone Thickness (Average Depth in Millimeters) | | | | | | |
|---|---|---|---|---|---|---|
| | Age | Frontal | Temporal Left/Right | Parietal | Coronal | Occipital |
| Mean | 36.5 | 9.06 | 7.0/7.06 | 9.66 | 15.6 | 14.9 |
| Range | 16–71 | 5–20 | 4–12/4–13 | 5–20 | 10–26 | 6–23 |

Stage 2

The scalp 38 is prepped and draped as in Stage 1. A fine needle (30 gauge) is inserted perpendicular to the skin, down to the implant 12. A skin-to-implant depth measurement is then made. The incision sites are again locally anesthetized with the same lidocaine solution. A #10 blade reopens the previous incision sites, down to the implants 12. The periosteum is cleared from the implant 12 and the healing cap is removed. An abutment 20 sized to extend slightly above the skin surface, preferably measuring 0.1 to 2.0 mm longer then the skin-to-implant depth, is then threaded into the threaded cavity 16 of the implant 12. The soft scalp tissue 38 is again closed in layers. A sufficient healing period is then allowed, preferably about 2–3 weeks.

Stage 3

Once all local inflammation has subsided, the abutments 20 will extend slightly above the skin surface (preferably about 0.1 to 2 mm). The patient's hair prosthesis 42 is placed on the head in its usual position. A skin marker is used to trace the position of the base of the prosthesis 42 on the scalp. The prosthesis 42 is removed and a moldable interface 40 of sufficient size is selected. The retention attachments 26 then are snapped into the abutments 20. The moldable interface 40 is softened in hot water and applied to the scalp and conformed to the shape of the scalp. While still cooling, the moldable interface 40 is trimmed to 1 to 2 mm inside the previous tracing, and the retention attachments 26 are adhered by crimping the interface 40 around the caps 30 and under the lips of the attachments 26. Once cooled, the interface 40 is removed from the patient's head with attachments 26 secured thereto. The attachments 26 may be further secured to the interface 40 with a glue such as a standard cyanoacrylate compound or more preferably a light cured acrylic. The light cured acrylic avoids a situation where the glue will interact with the skin causing potential irritation. There may also be a further advantage to adding another layer of the moldable interface material behind the location of the attachments 26 to reinforce the interface 40 against ripping. The hair-replacement prosthesis 42 is then sewn to the interface 40 or bonded with cyanoacrylate glue.

The preferred embodiment of the invention is now fully described. The above description, however, is only illustrative and is not intended to limit the invention in scope or spirit. Only the following claims and their equivalents limit the scope of the invention.

I claim:

1. An osseointegrated system for securing a hair prosthesis, comprising, in combination:
    a threaded implant post adapted for securing within the skull and adapted to receive an abutment after implantation;
    an abutment for attachment to said implant post, said abutment adapted to receive a retention attachment;
    a retention attachment capable of being removably secured to the abutment; and
    a moldable interface adapted for attachment to a hair prosthesis secured to the retention attachment.

2. The system of claim 1 wherein the implant post defines a threaded central cavity and the abutment includes a threaded portion that fits within said cavity.

3. The system of claim 1 wherein the retention attachment is secured to the abutment with a snap fit.

4. The system of claim 3 wherein the snap fit creates a ball and socket joint.

5. The system of claim 4 wherein the retention attachment includes a removable and replaceable ball-shaped end.

6. The system of claim 1 wherein the moldable interface is a synthetic mesh adapted to the shape of the head of the wearer.

7. The system of claim 1 wherein the moldable interface is a thermoplastic mesh that upon heating becomes moldable and hardens into molded shape upon cooling.

8. The system of claim 1 wherein the moldable interface is an integral part of the hair prosthesis.

9. The system of claim 1 wherein the retention attachment is secured to the interface with glue or a light cured acrylic.

10. The system of claim 9 wherein the glue is a cyanoacrylate compound.

11. The system of claim 1 wherein the interface is reinforced at an area where the retention attachment is secured.

12. The system of claim 11 wherein the reinforcement includes a second layer of the interface material.

13. A method of securing a hair prosthesis to a scalp, comprising attaching the hair prosthesis to an osseointegral mounting structure, wherein the installation of the mounting structure comprises the steps of:

mounting an implant post in the skull;

securing an abutment to the implant post after the implant post is mounted in the skull;

removably securing a retention attachment to the abutment;

fitting a moldable interface over the scalp and trimming it to the appropriate size and shape;

securing the retention attachment to the moldable interface; and attaching the hair prosthesis to the moldable interface on the side opposite the retention attachment.

14. The method of claim 13 wherein a plurality of osseointegral mounting structures are used.

15. The method of claim 14 wherein four osseointegral mounting structures are used.

* * * * *